(12) United States Patent
Cronshaw et al.

(10) Patent No.: US 6,393,141 B1
(45) Date of Patent: May 21, 2002

(54) APPARATUS FOR SURFACE IMAGE SENSING AND SURFACE INSPECTION OF THREE-DIMENSIONAL STRUCTURES

(75) Inventors: Anthony James Cronshaw, Stapleford; Mark Robson Humphries, Saffron Walden; Christopher James Hodges, Cambridge; John Horace Fisher, Herts, all of (GB)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/150,770

(22) Filed: Sep. 10, 1998

(51) Int. Cl.[7] .................................................. G06K 9/28
(52) U.S. Cl. ......................... 382/141; 382/312; 382/154
(58) Field of Search ................................. 382/154, 112, 382/285, 141, 142, 153, 126, 312, 318, 314, 324, 275; 250/223 B, 559.08; 348/37, 150, 98, 99, 103, 142; 345/425; 356/376, 239.4, 239.5, 240.1; 359/894, 196, 200, 205, 209, 230

(56) References Cited

U.S. PATENT DOCUMENTS 3,907,438 A 9/1975 Holeman .................... 356/156
4,874,940 A * 10/1989 McMeekin et al. ......... 250/223 B
4,972,091 A * 11/1990 Cielo et al. .................. 250/562
4,983,822 A * 1/1991 Fukuchi .................. 250/223 B
5,987,159 A * 11/1999 Nichani ....................... 382/141

FOREIGN PATENT DOCUMENTS

| DE | 4136326 A1 | 6/1992 |
| DE | 4126405 A1 | 2/1993 |
| EP | 526075 A2 | 2/1993 |
| EP | 583092 A1 | 2/1994 |

\* cited by examiner

Primary Examiner—Leo Boudreau
Assistant Examiner—Brian P. Werner
(74) Attorney, Agent, or Firm—Barry H. Jacobsen; Evan J. Federman

(57) ABSTRACT

An apparatus for providing a two-dimensional image of a three-dimensional object illuminates the surface of the object using an illumination source. Portions of the surface are imaged through an aperture in a plate onto a portion of a matrix sensor. The object is rotated about its principle axis while being simultaneously translated, and, at the same time the aperture is also rotated. By synchronizing these translational and rotational movements, successive portions of the object surface can image onto respective successive portions of the matrix sensor, thereby providing an improve two-dimensional image of the surface of the object.

12 Claims, 6 Drawing Sheets

APPARATUS FOR SURFACE IMAGE SENSING AND SURFACE INSPECTION OF THREE-DIMENSIONAL STRUCTURES

This invention relates to an apparatus for image sensing of three-dimensional structures for automatic inspection and other applications.

In a known imaging system, matrix cameras (i.e. areascan cameras) are used based on sensors such as a charge-coupled device (CCD) using a two-dimensional array of sensing elements. Matrix cameras are widely used in video cameras, closed circuit TV cameras (CCTV), and camcorders, and may be used to capture images of three-dimensional structures.

A problem with using a matrix camera is that only part of the three dimensional structure will be visible to the camera. For example, when imaging the surface of a cylinder or a sphere, the camera will only see the surface nearest the camera and will not be able to see the sides or back surfaces. This means that a multiple number of images will be needed to build up a complete all round image of the structure. In a practical application such as automatic inspection system, this is a disadvantage since capturing and processing multiple images imposes a heavier processing load, hence impacting system cost, than would be the case for a single image.

A second problem with using a matrix camera is that any non-flat areas of the structure will be projected onto the sensor in a distorted manner. For example, the walls of a cylindrical or spherical structure will produce distortion of the image as the surfaces curve away from the camera. This means that the image processing system must correct for this distortion when inspecting images containing surface detail, for example printed characters on the surface. This type of correction means significantly increased complexity and hence increased cost for the image processing system.

A third problem with using a matrix camera is that it becomes necessary to tile together multiple images. This applies where the surface being imaged contains patterns which may straddle two or more of the multiple images and it becomes necessary to tile (i.e. splice together) these images to reconstruct the complete image. This results in significant additional complexity in the image processing system and introduces the risk that spurious "splicing artefacts" may be created in the reconstructed image.

In another known image sensing system, a linescan camera is used to capture an image of a three dimensional structure. The linescan camera is arranged to form an image of a long narrow portion of the structure. After a suitable integration time which allows the image to be built up on the linescan sensor, the line image is read out of the camera in the form of a line of image pixels (i.e. picture elements) and transferred to an image storage and image processing system. The structure is arranged to move relative to the camera so that the process can be repeated on an adjacent long narrow portion of the structure, and eventually through a multiplicity of portions, a two-dimensional array of pixels is obtained.

A typical example of linescan imaging would be forming an image of a cylindrical surface whereby the cylindrical structure is arranged to rotate about its principle axis whilst a linescan camera captures a series of line images along the cylinder wall in direction parallel to the major axis.

A problem with linescan imaging is that it is optically inefficient. The camera's lens is capable of imaging an area wider than a narrow portion of the structure and illumination systems will also illuminate a wider portion of the structure. The linescan camera uses only a small part of the available image and discards the rest. This optical inefficiency leads to limitations in the overall imaging system, limiting the speed of image capture, and demanding added complexity of high intensity illumination.

A second problem with linescan imaging is image smearing (i.e. image blur). In a typical practical system, the structure is arranged to move at a constant speed relative to the camera so that successive lines of pixels are obtained at regular physical displacements around the structure. This means that any feature on the surface of the structure is moving relative to the camera and will tend to blur in the image to the extent of the integration time used by the camera. This will be most critical with fine detail on the surface of the structure, such as small dots or lines, whose size is similar to, or 1–5 times larger than, the size of the pixels being imaged at the structure. The overall effect of image smearing is that the quality of the captured image will be reduced with a loss of contrast and loss of image sharpness particularly affecting fine detail such as dots and lines.

In a known variant of linescan cameras—time delay integration (TDI) cameras—some of the problems of linescan imaging are overcome. In a TDI linescan camera, multiple parallel lines of pixels are imaged simultaneously. This means that the width of the imaged area is increased, for example to 8, 16, 32 or 96 parallel lines of pixels, depending on the particular imaging device used. In a TDI system, a shift register method is used to shift the image being integrated on the sensor such that the partially integrated image on the sensor tracks the movement of the structure. Hence each pixel in the read out will have been exposed for 8, 16, 32, or 96 clock periods. This increases the optical efficiency of the system.

A problem with TDI imaging is that image smear is still present for the same reasons as a basic linescan camera, leading to a loss of image sharpness and contrast on fine detail. A second problem with TDI cameras is their relatively high costs due to their specialised uses and consequent low volumes of manufacture.

A further problem with both normal linescan cameras and TDI linescan cameras is that imaging is restricted to applications where the camera can be focused on a line along the three dimensional structure. Given practical considerations of standard lenses and depth of field (for maintaining the image adequate sharpness of image), this mean that linescan systems are best suited to flat walled structures such as cylinders and are not well suited to more complex surfaces, for example, spherical structures.

According to the present invention, there is provided an apparatus for providing a two-dimensional representation of the surface of a three-dimensional object comprising means for translating the object along a path, and means for simultaneously rotating the object about at least one of its axes, means for sensing the two-dimensional representation, means for imaging a portion of the object surface onto a portion of the sensing means, the imaging means being translatable along a path parallel to the object path, the rates of translation of the object translating means and the imaging means, and of rotation of the object are selected so that the combination of the rotational and translational movement of the object and imaging means causes successive images of adjacent portions of the object surface to be imaged on successive portions of the sensing means, as the object travels along a portion of the object path, thereby capturing a two dimensional image of the surface of the object.

The invention will now be described, by way of example only, with reference to the accompanying drawings, of which:

Figure 1:
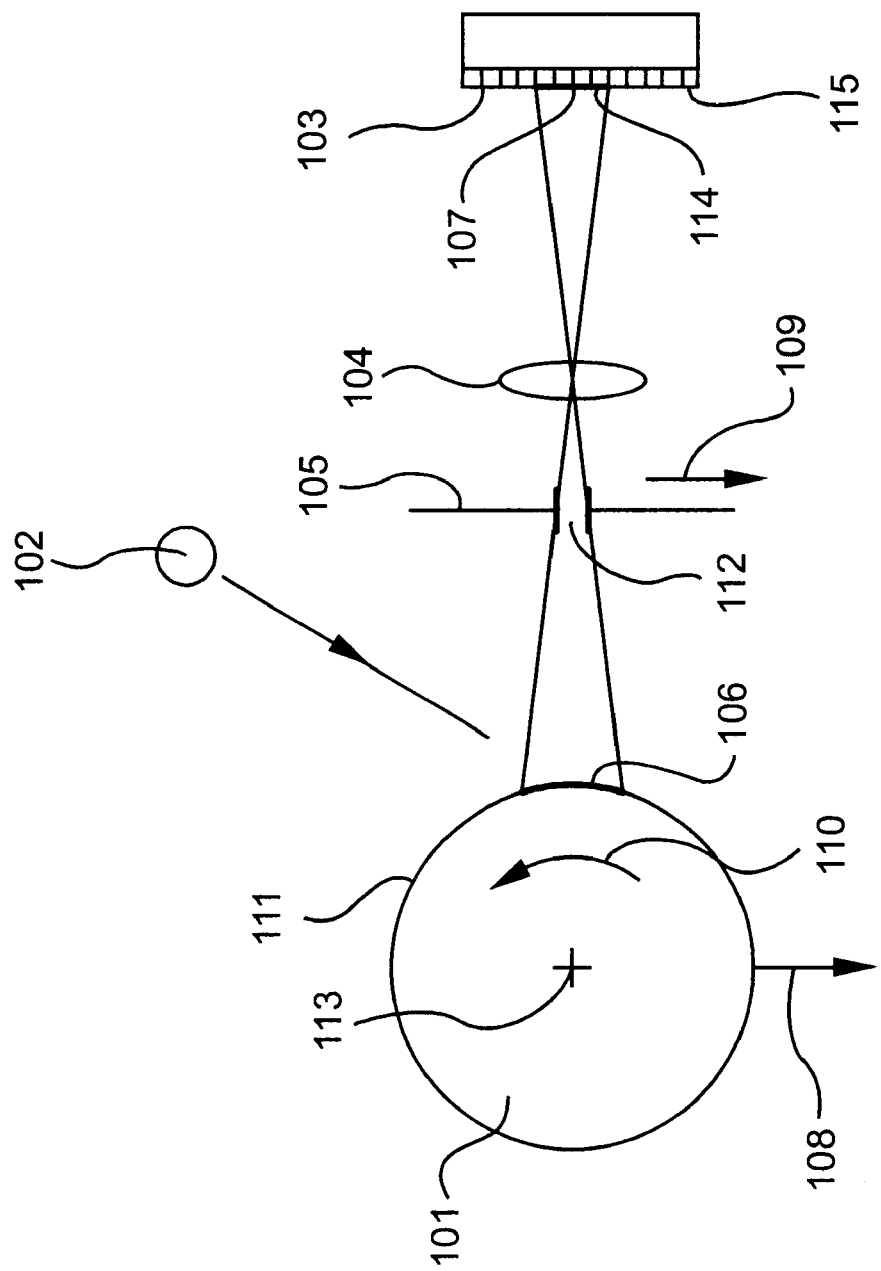
FIG. 1 is a schematic cross sectional view of an embodiment of the present invention for sensing the surface of a cylinder.
Figure 2:
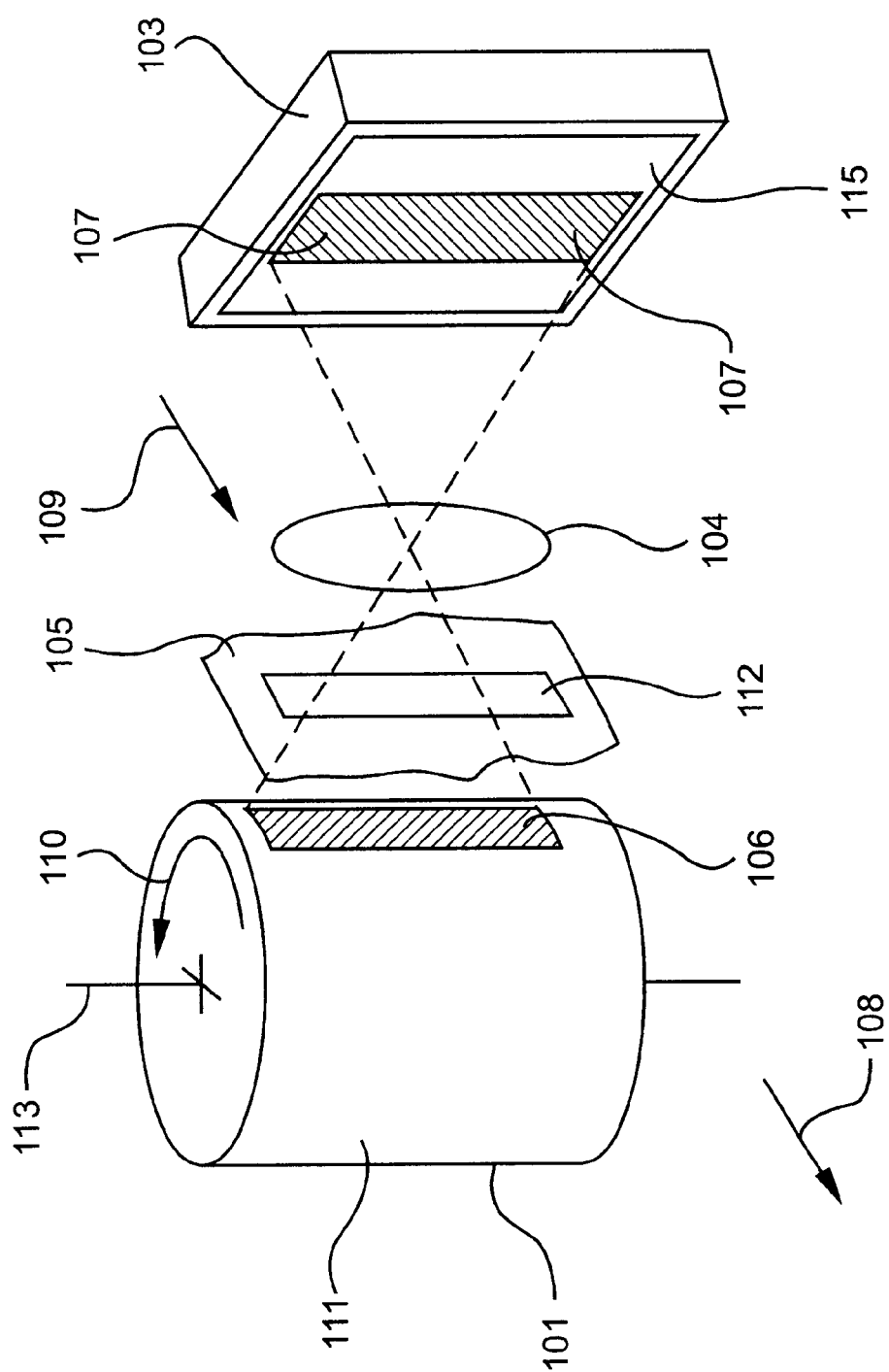
FIG. 2 is a schematic perspective view of the embodiment of FIG. 1.
Figure 3A:
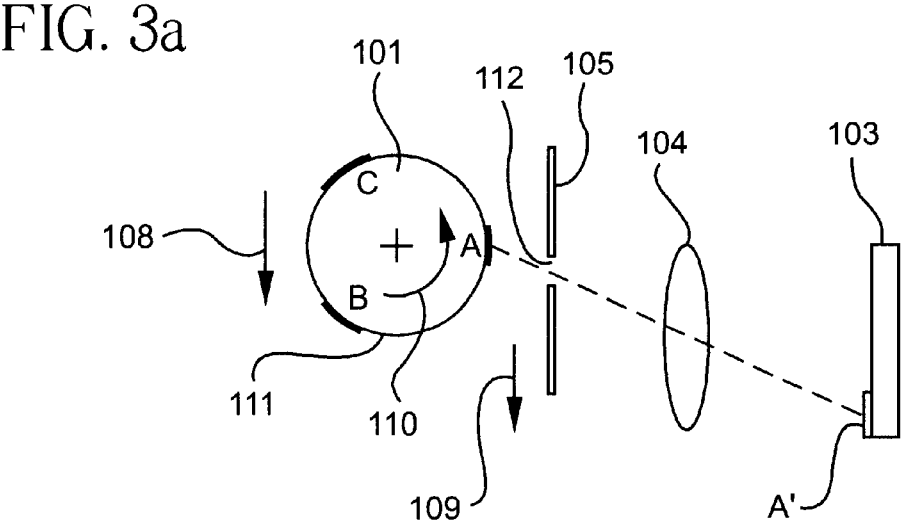
Figure 4:
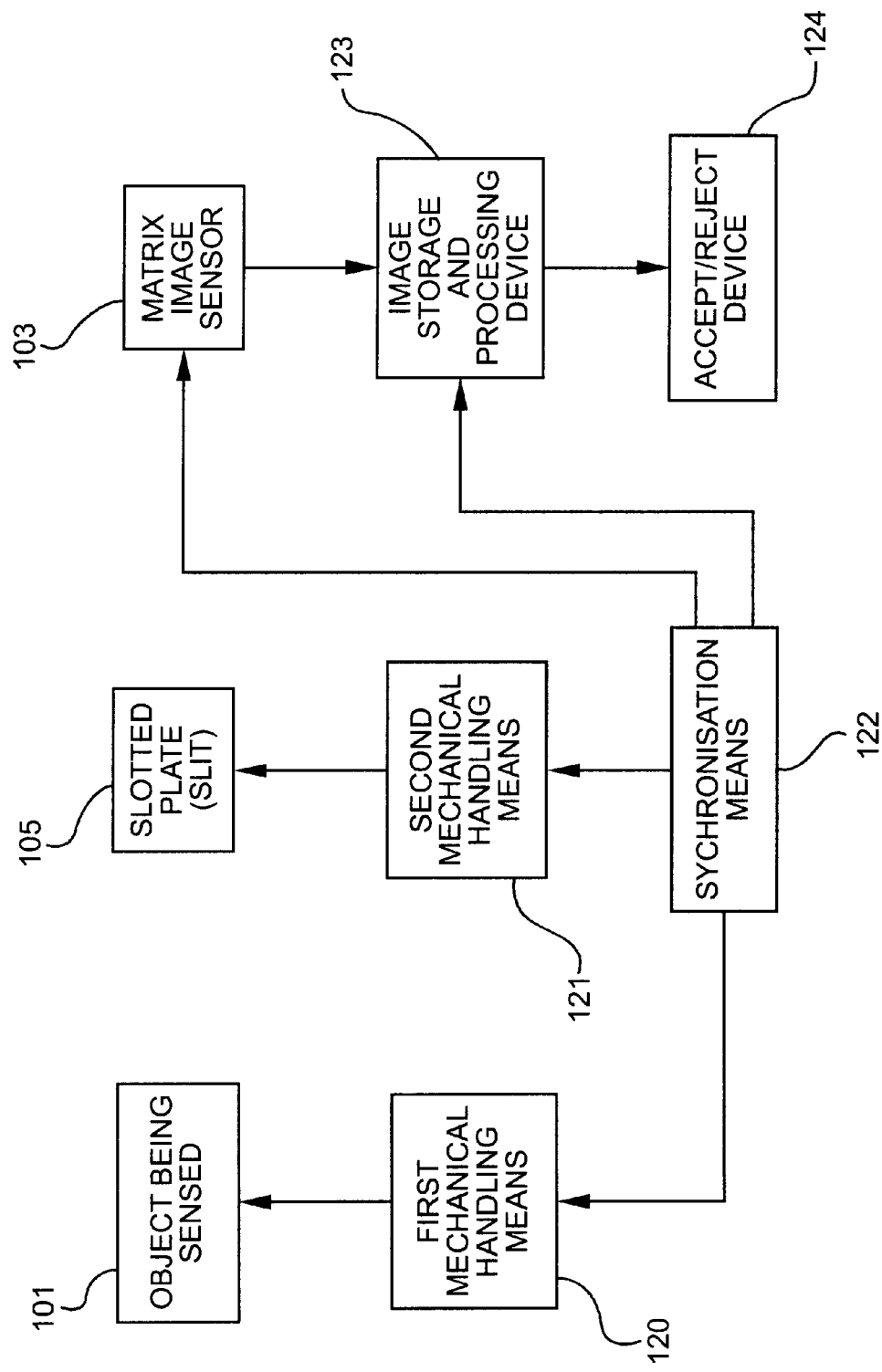
Figure 5:
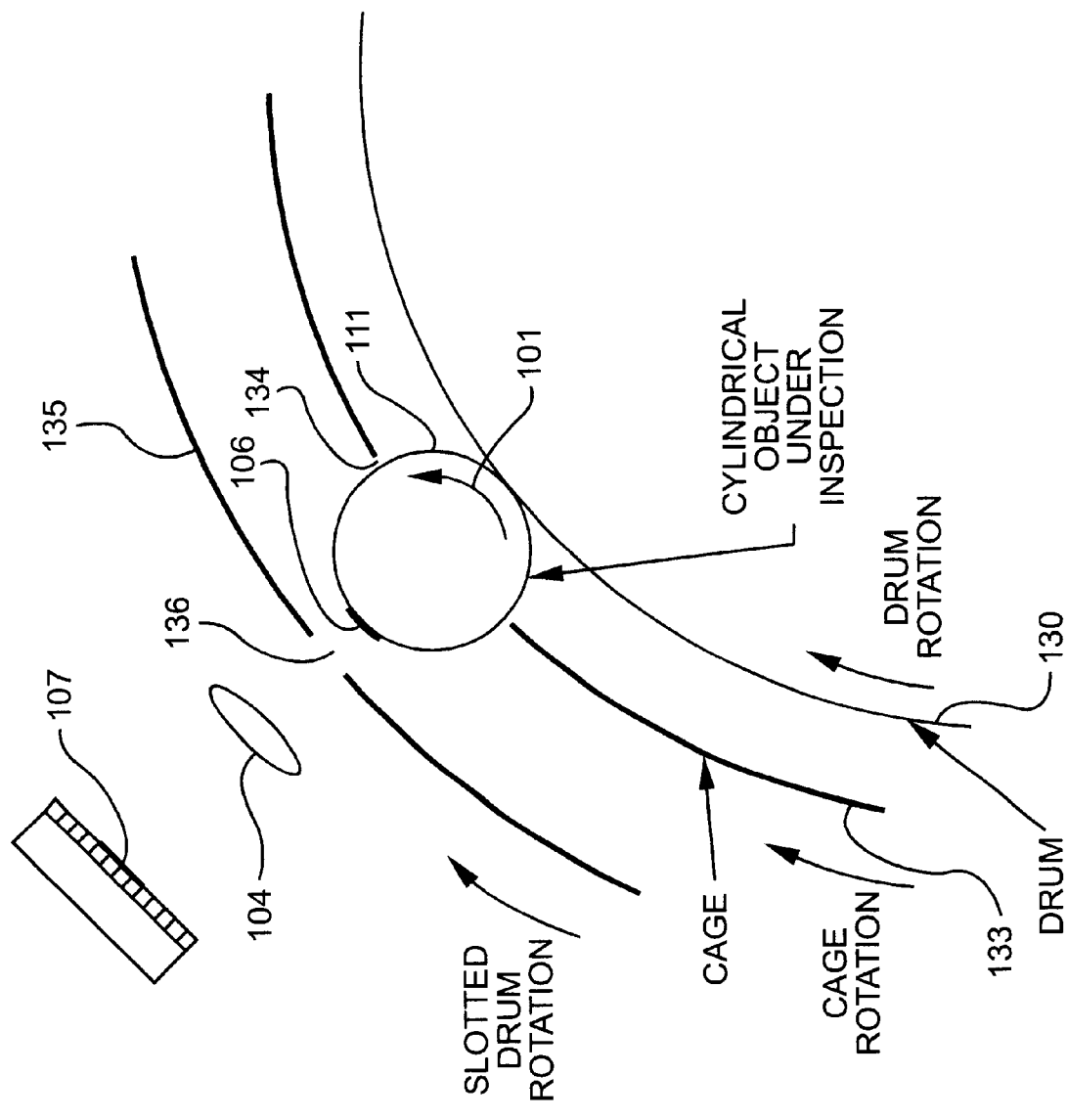
Figure 6:
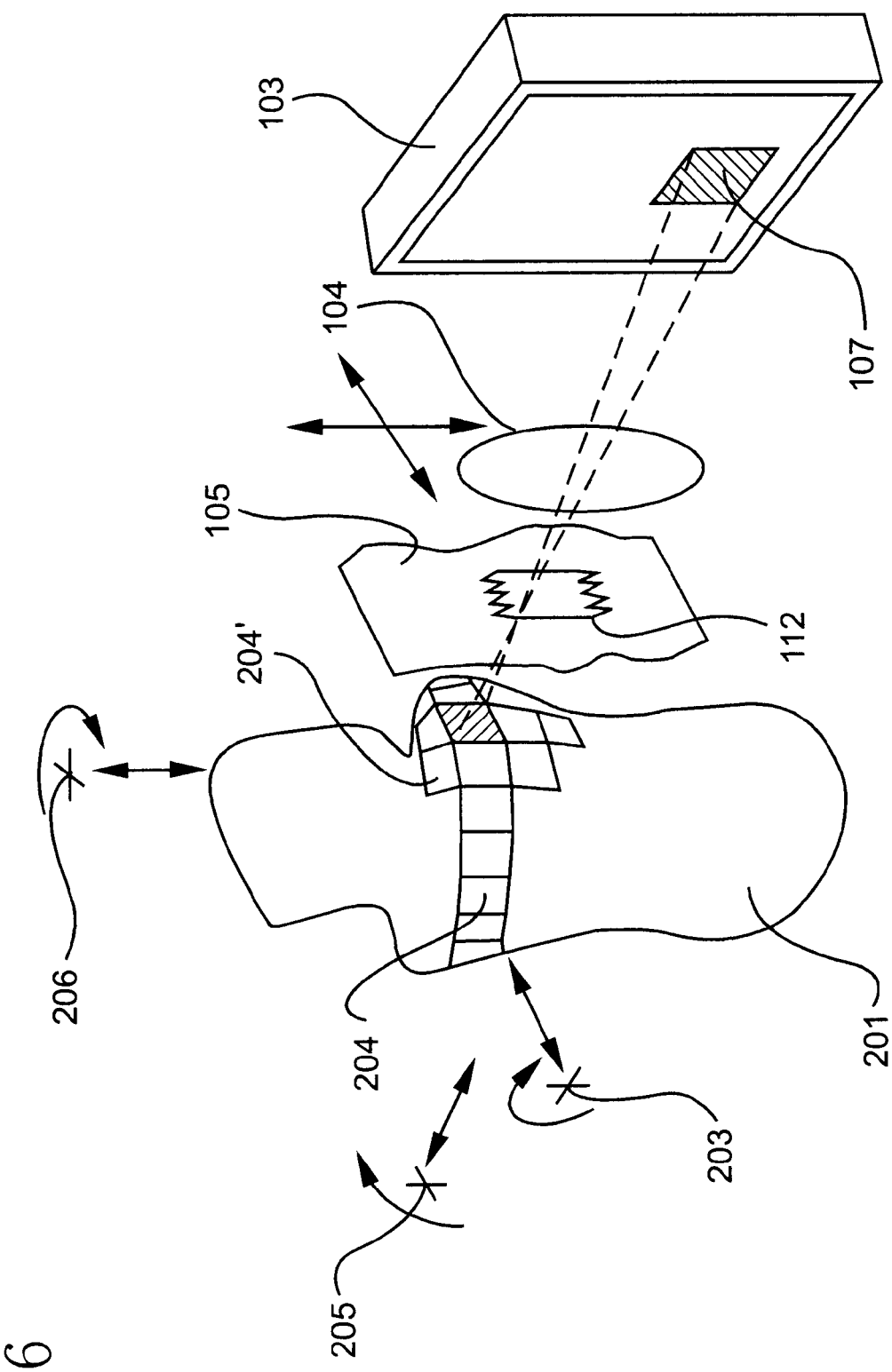

FIGS. 3(a), (b) and c) are a series of schematic cross sectional diagrams to illustrate how the embodiment of FIGS. 1 and 2 is used to build up an image over time;

FIG. 4 is a schematic block diagram illustrating the major steps in the operation of the embodiment of FIGS. 1 and 2, for automatic inspection of an article;

FIG. 5 is a schematic vertical cross section diagram through section of an embodiment of the mechanical handling means, used for handling an article being inspected; and FIG. 6 is a schematic perspective view of another embodiment for image sensing of complex non-cylindrical structures.

Referring to FIGS. 1 and 2, a cylindrical object 101, is illuminated by a light source 102, so that portion 106 of the cylinder surface 111 is illuminated. A matrix image sensor 103 receives the image 114 of the portion 106, on a portion 107 of the sensor surface 115, via lens 104, and via an aperture 112 in a plate 105. The aperture 112 is an elongate, parallel-sided aperture 112 that has a longitudinal axis that is substantially parallel to the principle axis of the cylinder 101. Hence the portion 106 of the cylinder surface 111 that is to be imaged onto the matrix sensor 103, is a long and relatively narrow portion lying along the side of the cylinder 101 in a direction substantially parallel to the cylinder's principle axis 113. Furthermore, the image 114, received by the matrix sensor 103, is also a long and relatively narrow image portion 107 corresponding to the illuminated portion 106.

The entire cylindrical surface 111 of the object 101, is scanned, and, therefore imaged by the matrix sensor 103, by arranging for simultaneous mechanical translation and rotation of the object 101, and, at the same time, mechanical translating of the plate 105, whilst arranging for the matrix sensor 103, to have its field integration period synchronised to this cycle of mechanical translation and rotation.

The details of this mechanical cycle are as follows:

The cylindrical object 101 is arranged to translate at a substantially linear speed 108, whilst simultaneously rotating with rotary speed 110. The rotary speed 110 is arranged so that the instantaneous surface speed of the imaged portion 106 is substantially zero relative to the lens 104 and matrix sensor 103. At the same time, the plate 105—and therefore the aperture 112—is arranged to translate at a linear speed 109, so that the center of the illuminated portion 106, the aperture 112, and the center of the lens 104, remain substantially collinear.

Figure 3B:
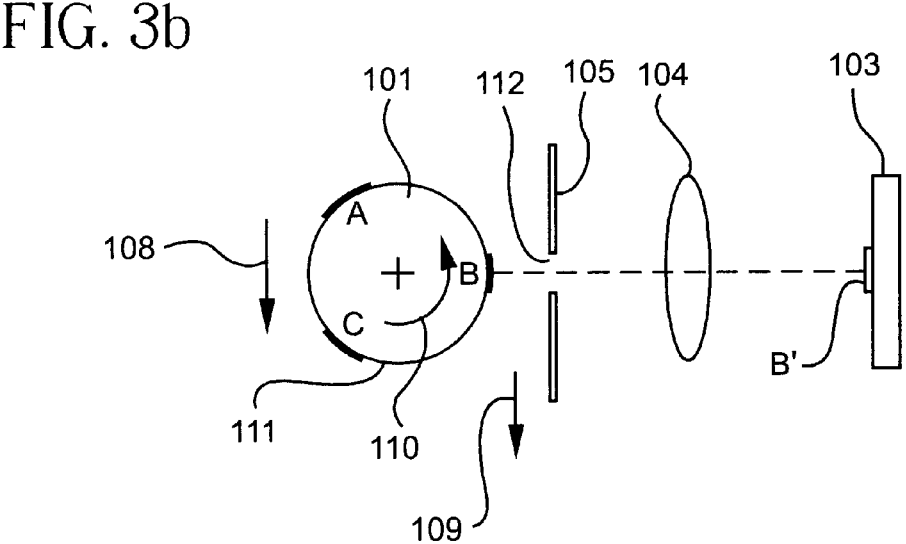
Figure 3C:
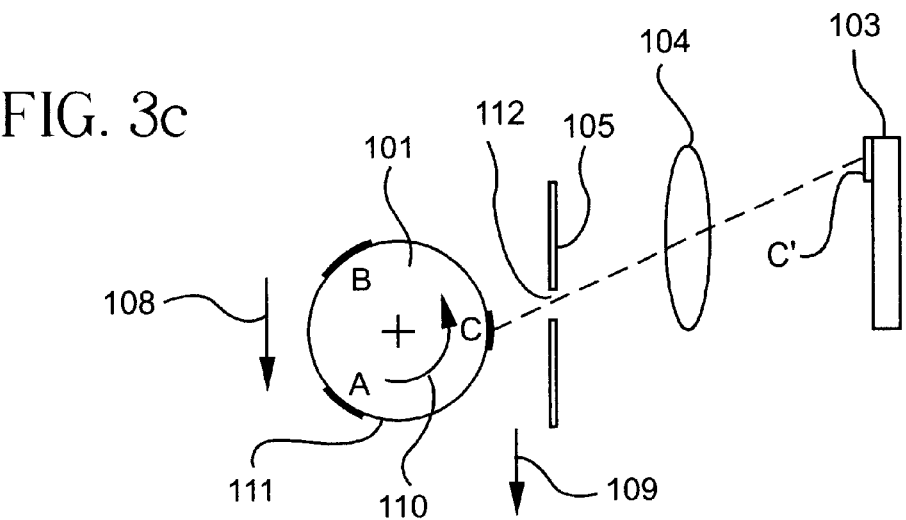

By rotating and translating the cylinder 101, and translating the aperture 112, the whole surface 111 of the cylinder 1 can be imaged onto the matrix sensor 103. FIG. 3 illustrates how this is achieved. The matrix sensor 103 is reset at time Ta, at which moment the cylinder surface 111 is illuminated. A portion A of this cylinder surface III is then imaged onto a corresponding portion A' on the matrix sensor 103 through the aperture 12, which is in a first position. The matrix sensor 103 is held in a continuous integration mode for the rest of the cycle whilst the cylinder 101 progressively rotates and progressively images further portions of the surface 111, for example portion B at time Tb, and portion C at time Tc onto respective portions B' and C' on the matrix sensor surface 115. These respective portions B', C' are spatially separated because of the simultaneous translation of the aperture 112. Once a revolution of the cylinder 101 has been completed, portion A will once again be sensed.

By carrying out this combination of rotation and translation, successive portions of the cylinder surface 111 are imaged onto corresponding successive portions of the matrix sensor 103, and, therefore, the overall effect of these mechanical and sensor arrangements is that the surface of the cylinder is exposed on a continuous incremental basis around the cylinder wall and that a matching image of the surface is received on a continuous incremental basis at the matrix sensor 103.

To carry out scanning of the whole surface in an automated application, an apparatus can be operated in accordance with the stepS set out in FIG. 4. The object to be scanned and imaged, i.e. the cylinder 101 described above is rotated and translated by a first mechanical handling means 120, and the plate 105 is translated by a second mechanical handling means 121. The first and second mechanical handling means 120,121 are synchronised together by a synchronisation means 122 so that collinearity of the required imaged portion 106, the aperture 106 and the center of the lens 104 is maintained. The synchronisation means 122 also controls the exposure cycle of the matrix sensor 103 so that a reset is applied at the start of a new cycle and the exposure is held throughout the rest of the cycle whilst the required cylinder surface 111 is sensed.

FIG. 5 illustrates a mechanical embodiment for an apparatus for scanning an object, such as a cylinder, as described above.

The translation and rotation of the cylinder 101 and aperture 112 are carried out as follows:

The cylinder 101 is freely mounted, for rotation about its principal, longitudinal axis, on a cylindrical cage 133, and its surface 111 rests on a cylindrical drum 130 which is made to rotate about its principle axis (not shown), in the direction of the arrow in FIG. 5. The outer surface 131 of the drum 130 is in contact with the cylinder surface 111 so that, as the drum 130 rotates it imparts a rotational force to the cylindrical cage 133 causing it to rotate. This also illustrated by the arrows in FIG. 5. The cylinder 101 is contained by an aperture 134 in the cylindrical cage. The cage 133 is made to rotate about its principle axis, which coincides with the drum's principle axis. A slotted drum 135, also made to rotate about its principle axis coinciding with the other previously mentioned axes, implements the function of the plate 105 as described earlier, with an aperture 136 in the slotted drum 135 corresponding to the aperture 112 described above, and the rotation of the slotted drum 135 effects the translation of the aperture 136. The cylindrical drum 130 and cage 133—along with its associated drive means—corresponds to the first mechanical handling means.

The slotted drum 135 is rotated by the second handling means 121. Mechanical drives, for example motors and gearing known to persons skilled in the art, can then easily be arranged to couple the three rotating elements (friction drum 130, cage 133 and slotted drum 135) in a synchronised manner to produce the required rotation of the object under inspection. Electrical devices, for example rotary encoders as known to persons skilled in the art, can easily be arranged to synchronise the mechanical cycle with the camera exposure. The two-dimensional image captured by the matrix sensor 103 is then processed using any suitable image processing technique in an image storage and processing device 123. If the image is used to compare it to a reference image, then an accept/reject device 124 can be used to accept or reject the object if it varies with the reference image.

Referring to FIG. 6, a further preferred embodiment of the present invention is shown illustrating that the invention is not restricted to image sensing of cylindrical structures, but can extend to many other shapes of three dimensional structures. To sense a more complex three-dimensional structure such as that illustrated in FIG. 6, the structure 201 is scanned in a horizontal direction to generate a number of imaged sections 204, each section being in the form of a horizontal stripe, each stripe being scanned sequentially in a vertical direction, that is by firstly scanning in a horizontal direction, and then moving vertically to scan horizontally again along an adjacent vertical stripe 204', and so on, until all the structure is scanned and imaged, thereby building up a complete image of the structure 201. The actual method of "unwrapping" the surface to provide the image is the same as described above, but, in this case, a number of "unwrapped" images are then combined to produce the final image of the whole of the surface. In this respect, the aperture plate 105 moves not only in a horizontal direction, but must be able to move in a vertical direction as well, in order to sequentially scan in the vertical direction. In order to scan more complex structures, the structure 201 needs to be rotated and translated about, and along, more axes than with the first embodiment described above. For the more complex structures, there will be rotation about three orthogonal axes 203,205, 206, as illustrated in FIG. 6, as well as translation along theses axes. For a less complex structure, for example, a cone or stepped cylinder, the structure need not be rotated and translated about, and along, all these axes. In FIG. 6, the aperture plate 105 has a square or rectangular aperture 112 with feathered top and bottom edges. The feathered edges blurs the edges of the image of the sections 204 by building a transition boundary between the image and the surrounding pixels so that the image gradually fades out at the edge. Thus, when two adjacent horizontal imaged sections are processed together, the overlapping edges of adjacent stripes are free of sudden gaps or double exposure overlaps.

It will be obvious to persons skilled in the art, that various modifications are possible within the scope of the present invention. For example, any suitable image processing technique can be used, as well as other suitable image sensors. The translation and rotation of the various components can be effected by any suitable means.

What is claimed is:

1. An apparatus for providing a two-dimensional representation of the surface of a three-dimensional object comprising:
   means for translating the object along a path, and means for rotating the object about at least two axes;
   means for sensing the two-dimensional representation,
   means for imaging a portion of the object surface onto a portion of the sensing means,
   the imaging means being translatable along two directions, the rates of translation of the object translating means and the imaging means, and of rotation of the object are selected so that the combination of the rotational and translational movement of the object and imaging means causes successive images of adjacent portions of the object surface to be imaged on successive portions of the sensing means on a continuous incremental basis, as the object travels along a portion of the object path, thereby capturing a two dimensional image of the surface of the object.

2. An apparatus according to claim 1, wherein the apparatus further includes means for comparing the captured image to a reference image so as to detect deviations in the object's surface from that of the reference image, and to thereby accept or reject the object on the basis of this comparison.

3. An apparatus according to claim 1, wherein the object path is an arcuate path, and the object is rotatable around its longitudinal axis.

4. An apparatus according to claim 1, further comprising means for synchronizing the translation and rotation of the object, the translation of the imaging means, and the speed of operation of the sensing means to provide the two-dimensional representation.

5. An apparatus according to claim 1, wherein the sensing means is operable to receive the imaged portion of the object surface and to provide a signal representative of the image, the apparatus further comprising means, coupled to the sensing means, for processing the signal from the sensing means.

6. An apparatus according to claim 5, wherein the image processing means includes an image storage means.

7. An apparatus according to claim 1, wherein the imaging means comprises a mask means with a narrow rectangular aperture provided therein.

8. An apparatus according to claim 1, wherein the imaging means comprises a mask means with an aperture with feathered top and bottom edges provided therein.

9. A method for generating a two-dimensional representation of the surface of a three-dimensional object, the method comprising the steps of: translating the object along a path, whilst simultaneously rotating the object about a first axis;
   translating the object along a path, whilst simultaneously rotating the object about a second axis;
   imaging a portion of the object surface, by means of an imaging means, onto a portion of a means for sensing the two-dimensional representation;
   translating the imaging means along a first direction by means of an object translating means;
   translating the imaging means along a second direction by means of the object translating means; and
   selecting the rates of translation of the object translating means and the imaging means, and of rotation of the object so that the combination of the rotational and translational movement of the object and imaging means causes successive images of adjacent portions of the object surface to be imaged on successive portions of the sensing means, on a continuous incremental basis, as the object travels along a portion of the object path, thereby capturing a two dimensional image of the surface of the object.

10. A method according to claim 9, further comprising the steps of comparing the captured image to a reference image to detect deviations in the object's surface from that of the reference image, and accepting or rejecting the object on the basis of this comparison.

11. A method according to any preceding claim, wherein the object path is an arcuate path, and the object is rotated around its longitudinal axis.

12. A method according to claim 9, further comprising the step of synchronizing the translation and rotation of the object, the translation of the imaging means, and the speed of operation of the sensing means to provide the two-dimensional representation.

* * * * *